(12) United States Patent
Sakamoto

(10) Patent No.: US 7,977,503 B2
(45) Date of Patent: Jul. 12, 2011

(54) POLYMERIZATION INHIBITION METHOD

(75) Inventor: Kazuhiko Sakamoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/452,018

(22) PCT Filed: Jun. 4, 2008

(86) PCT No.: PCT/JP2008/060295
§ 371 (c)(1),
(2), (4) Date: Dec. 11, 2009

(87) PCT Pub. No.: WO2008/152960
PCT Pub. Date: Dec. 18, 2008

(65) Prior Publication Data
US 2010/0130766 A1    May 27, 2010

(30) Foreign Application Priority Data

Jun. 13, 2007 (JP) .................... 2007-156644

(51) Int. Cl.
*C07C 69/00* (2006.01)
*C07C 51/16* (2006.01)

(52) U.S. Cl. ........................................... 560/4; 562/542
(58) Field of Classification Search .................. None
See application file for complete search history.

(56) References Cited

U.S. PATENT DOCUMENTS

| | | | | |
|---|---|---|---|---|
| 3,503,856 A | * | 3/1970 | Blackmore | 205/69 |
| 3,877,931 A | * | 4/1975 | Neskora et al. | 75/370 |
| 5,856,568 A | | 1/1999 | Okamoto et al. | |
| 2001/0050217 A1 | * | 12/2001 | Uehara et al. | 203/8 |
| 2003/0095471 A1 | | 5/2003 | Hamamoto et al. | |
| 2004/0015014 A1 | | 1/2004 | Nishimura et al. | |

FOREIGN PATENT DOCUMENTS

| | | |
|---|---|---|
| JP | 6-211735 | 8/1994 |
| JP | 9-95465 | 4/1997 |
| JP | 2003-103155 | 4/2003 |
| JP | 2003-128646 | 5/2003 |
| JP | 2004-51489 | 2/2004 |

OTHER PUBLICATIONS

International Search Report dated Aug. 12, 2008 issued in connection with International (PCT) Application No. PCT/JP2008/060295.

* cited by examiner

*Primary Examiner* — Daniel Sullivan
*Assistant Examiner* — Jennifer C Sawyer
(74) *Attorney, Agent, or Firm* — Wenderoth, Lind & Ponack L.L.P.

(57) ABSTRACT

The objective of the present invention is to provide a method for inhibiting polymerization of (meth)acrylic acid and the like. By the method, the generation of deposit in a pipe, which is exclusively used for providing a solution of a dialkyldithiocarbamic acid copper salt to a distillation column and the like, is prevented, and the problems such as the clogging of the pipe and polymerization in the distillation column are solved. The method according to the present invention for inhibiting polymerization of (meth)acrylic acid and/or an ester thereof is characterized in comprising a step of inhibiting polymerization of (meth)acrylic acid and/or the ester thereof by using a solution of a dialkyldithiocarbamic acid copper salt dissolved in an organic solvent, wherein a content amount of copper sulfate in the solution of the dialkyldithiocarbamic acid copper salt is 100 ppm or less by mass.

4 Claims, No Drawings

POLYMERIZATION INHIBITION METHOD

TECHNICAL FIELD

The present invention relates to a method for inhibiting polymerization of (meth)acrylic acid and/or an ester thereof.

BACKGROUND ART (Meth)acrylic acid is produced generally by introducing a (meth)acrylic acid-containing gas obtained by vapor-phase contact oxidation reaction into a condensation tower or a collection tower to obtain an aqueous (meth)acrylic acid solution and further purifying the solution. An ester of (meth) acrylic acid is produced by esterifying purified (meth)acrylic acid or crude (meth)acrylic acid at proper timing and carrying out purifying based on the necessity. As a purification method of (meth)acrylic acid and/or an ester thereof (hereinafter, referred to as "(meth)acrylic acid and the like"), a method in which an aqueous solution of (meth)acrylic acid and the like is introducing into an azeotropic separation tower and is subjected to azeotropic distillation in the presence of an azeotropic solvent has been known well. However, (meth)acrylic acid or the like is very easily polymerized. Therefore, particularly in high temperature facilities such as an azeotropic separation tower and a distillation tower, a polymerization inhibitor to prevent the polymerization of (meth)acrylic acid and the like is employed.

It has been well known that a dialkyldithiocarbamic acid copper salt alone or in combination with another polymerization inhibitor is used as the polymerization inhibitor used in the production process for (meth)acrylic acid and the like, as disclosed in JP-A No. 2003-103155, JP-A No. 6-211735 and JP-A No. 9-95465.

DISCLOSURE OF THE INVENTION

As mentioned above, a dialkyldithiocarbamic acid copper salt is used alone or in combination with another polymerization inhibitor such as phenothiazine, as a polymerization inhibitor. In such a case, the dialkyldithiocarbamic acid copper salt is dissolved in organic solvent such as toluene. Subsequently, the solvent is generally carried to distillation column and the like through an exclusive pipe.

In a case where the carriage of the solution of a dialkyldithiocarbamic acid copper salt is continued, deposit is generated in a pipe and the like, and the problem of clogging is likely to occur. In addition, the amount of the dialkyldithiocarbamic acid copper salt provided to a distillation column and the like is decreased by the clogging in the pipe; as a result, polymerization in the distillation column and the like would not be prevented.

Under the above-mentioned situation, the objective of the present invention is to provide a method for inhibiting polymerization of (meth)acrylic acid and the like. By the method, the generation of deposit in a pipe, which is exclusively used for providing a solution of a dialkyldithiocarbamic acid copper salt to a distillation column and the like, is prevented, and the problems such as the clogging in the pipe and polymerization in the distillation column are solved.

The inventors of the present invention studied the generation of the above deposit. As a result, the inventors found that the deposit is attributed to copper sulfate, which is inevitably contained in a dialkyldithiocarbamic acid copper salt as impurity. The inventors therefore found that the above objective can be achieved by decreasing the content amount of copper sulfate in the solution of a dialkyldithiocarbamic acid copper salt, to complete the present invention.

The method according to the present invention for inhibiting polymerization of (meth)acrylic acid and/or an ester thereof is characterized in comprising a step of inhibiting polymerization of (meth)acrylic acid and/or the ester thereof by using a solution of a dialkyldithiocarbamic acid copper salt dissolved in an organic solvent, wherein a content amount of copper sulfate in the solution of the dialkyldithiocarbamic acid copper salt is 100 ppm or less by mass.

BEST MODE FOR CARRYING OUT THE INVENTION

The dialkyldithiocarbamic acid copper salt used in the present invention method is specifically exemplified by dimethyldithiocarbamic acid copper salt, diethyldithiocarbamic acid copper salt, dipropyldithiocarbamic acid copper salt and dibuthyldithiocarbamic acid copper salt. The salts can be used alone or in combination with each other.

The organic solvent for dissolving the above dialkyldithiocarbamic acid copper salt is not limited; and any solvent, which is generally used for preparing the solution of the dialkyldithiocarbamic acid copper salt as the polymerization inhibitor for (meth)acrylic acid and the like, can be used as the organic solvent. The organic solvent includes, for example, aromatic hydrocarbons such as toluene; aliphatic hydrocarbons such as heptane, 1-heptene, methylcyclohexane, cycloheptene, cycloheptadiene, cycloheptatriene, 2,4-dimethyl-1, 3-pentadiene, methylcyclohexene, methylcyclohexane; esters such as methyl acrylate, ethyl acrylate, buthyl acrylate, 2-ethylhexyl acrylate, methyl methacrylate, n-propyl acetate, vinyl acrylate, allyl acetate, isopropenyl acetate, vinyl propionate, methyl crotonate; and ketones such as diethyl ketone, methyl propyl ketone, methyl isobutyl ketone, methyl tertbutyl ketone. The above solvents may be industrial organic solvents; and are not necessarily required to be pure products and may contain impurities and organic solvent other than the above organic solvents unless polymerization prevention capability of a dialkyldithiocarbamic acid copper salt is deteriorated or the above-mentioned precipitates are generated. For example, a mixed solution which is obtained in (meth) acrylic acid production process or the like and contains the above organic solvent may be used as it is. For example, a circulation solution of a distillation tower may be used as an organic solvent for dissolving a dialkyldithiocarbamic acid copper salt.

In the method of the present invention, the content of copper sulfate in the dialkyldithiocarbamic acid copper salt solution is adjusted to 100 ppm by mass or lower. If the copper sulfate content exceeds 100 ppm, problems such as generation of precipitates in a solution sending pipe may occur. The copper sulfate content is adjusted to be preferably 90 ppm or lower and more preferably 50 ppm or lower.

Copper sulfate exists as a monohydrate, a trihydrate and a pentahydrate besides anhydride, and it cannot be specified whether the copper sulfate existing in a dialkyldithiocarbamic acid copper salt is anhydride or any of hydrates. It is therefore difficult to determine the ratio of copper sulfate in a dialkyldithiocarbamic acid copper salt and it is also difficult to determine the ratio of copper sulfate in a solution in which the copper salt is dissolved. In addition, the copper ions in the dialkyldithiocarbamic acid copper salt solution cannot be distinguished whether the ion is derived from a dialkyldithiocarbamic acid copper salt or from cupper sulfate. Therefore, the copper sulfate content in a dialkyldithiocarbamic acid copper salt solution is difficult to be measured directly. Consequently, the content of the copper sulfate in a dialkyldithiocarbamic acid copper salt solution can be determined by, for example, the following procedure, since a dialkyldithiocarbamic acid copper salt is insoluble in water and contrarily copper sulfate is water-soluble.

A dialkyldithiocarbamic acid copper salt to be used is washed well with water to obtain a washing solution.

The copper ion concentration in the obtained washing solution is measured.

It is assumed that the copper sulfate existing in the dialkyldithiocarbamic acid copper salt is pentahydrate, and the copper sulfate content ratio in the dialkyldithiocarbamic acid copper salt is calculated from the measured value of the copper ion concentration and the amount of the washing solution.

The copper sulfate content in the solution is calculated from the content ratio of the copper sulfate in the dialkyldithiocarbamic acid copper salt and the concentration of the dialkyldithiocarbamic acid copper salt solution to be used.

On the other hand, when the content of copper sulfate in the present invention method is too low, the concentration of a dialkyldithiocarbamic acid copper salt solution sometimes becomes low. As a result, it may become needed to increase the use amount of the solution, that is, the flow rate of the solution, for preventing polymerization. In such a case, it is required to heighten the capacity of a supply pump for the polymerization prevention solution and the process may possibly become rather complicated. In addition, when it is intended to lower the copper sulfate content in the solution while the polymerization prevention capability is kept by using the highly pure dialkyldithiocarbamic acid copper salt in which the copper sulfate content is low, the cost may possibly be increased to an excess extent. Therefore, the lower limit of the copper sulfate content in a dialkyldithiocarbamic acid copper salt solution is preferably 1 ppm by mass or higher and more preferably 5 ppm by mass or higher.

A method for adjusting the copper sulfate content in a dialkyldithiocarbamic acid copper salt solution to 100 ppm or lower is not particularly limited. For example, the copper sulfate content in a dialkyldithiocarbamic acid copper salt may be previously adjusting, or the concentration of the solution may be adjusted so that the copper sulfate content in the dialkyldithiocarbamic acid copper salt solution becomes 100 ppm or lower.

In the present invention, the content amount of copper sulfate in the solution of the dialkyldithiocarbamic acid copper salt is adjusted to 100 ppm or less. In addition, the concentration of the dialkyldithiocarbamic acid copper salt in the solution is preferably 0.1% or more by mass and 10% or less by mass, more preferably 1% or more by mass and 5% or less by mass, for effectively preventing the polymerization of (meth)acrylic acid and the like.

In the present invention method, the polymerization of (meth)acrylic acid or the like is prevented by supplying a dialkyldithiocarbamic acid copper salt solution at the time of producing the (meth)acrylic acid or the like. Specifically, for example, in (meth)acrylic acid production process, a (meth)acrylic acid-containing gas obtained by vapor-phase contact oxidation is introduced into a condensation tower or a collection tower to obtain an aqueous (meth)acrylic acid solution. Next, the aqueous (meth)acrylic acid solution is introduced into an azeotropic separation tower, and roughly purified (meth)acrylic acid is obtained by azeotropic distillation in the presence of an azeotropic solvent. The roughly purified (meth)acrylic acid is further introduced into a distillation tower to be finely purified. In the above-mentioned process, a dialkyldithiocarbamic acid copper salt solution is supplied to one or more of the condensation tower, collection tower, azeotropic separation tower and distillation tower to prevent the polymerization of (meth)acrylic acid in the respective towers. In the case of a (meth)acrylic acid ester, the dialkyldithiocarbamic acid copper salt solution is similarly supplied in an esterification step or a purification step to prevent the polymerization.

Specific supply means of a dialkyldithiocarbamic acid copper salt solution is not particularly limited. For example, a dialkyldithiocarbamic acid copper salt solution is prepared in a tank equipped with a mixer, a surface level detector, a dialkyldithiocarbamic acid copper salt-throwing inlet, an organic solvent inlet and a dialkyldithiocarbamic acid copper salt solution supply port, and the dialkyldithiocarbamic acid copper salt solution may be supplied through an exclusive pipe by a solution sending pump, as described in JP-A No. 2003-103155.

The supply amount of a dialkyldithiocarbamic acid copper salt solution may be properly adjusted. For example, it is preferable to supply the solution so that the amount of a dialkyldithiocarbamic acid copper salt to be supplied to a distillation tank is set to about 1 to 100 ppm by mass relative to the evaporation amount of (meth)acrylic acid and the like.

In the present invention method, general polymerization inhibitor which is used in the production process of (meth)acrylic acid and the like may be used in addition to a dialkyldithiocarbamic acid copper salt. For example, polymerization inhibitors such as phenothiazine, manganese acetate and hydroquinone may be provided in addition to a dialkyldithiocarbamic acid copper salt to a distillation column and the like through a pipe else besides the pipe for the dialkyldithiocarbamic acid copper salt. In addition, molecular oxygen may be provided from the bottom of a distillation column at the same time.

In the present invention, a (meth)acrylic acid ester includes, for example, methyl acrylate, ethyl acrylate, buthyl acrylate, 2-ethylhexyl acrylate, 2-hydroxyethyl acrylate, 2-hydroxypropyl acrylate, methyl methacrylate, ethyl methacrylate, buthyl methacrylate, 2-hydroxyethyl methacrylate and 2-hydroxypropyl methacrylate.

According to the method of the present invention, the copper sulfate content in a dialkyldithiocarbamic acid copper salt solution is adjusted to 100 ppm by mass or lower, so that the generation of precipitates in a pipe can be efficiently suppressed even if the transportation of the solution is carried out for a long duration. As a result, stable supply of the polymerization inhibitor is made possible and the production of polymers can be suppressed and also the production of (meth)acrylic acid and the like can be stably continued.

EXAMPLES

The present invention is further described in detail with reference to the following examples, which corresponds to preferable embodiments of the present invention.

Example 1

A gas mixture was obtained by vapor-phase contact oxidation of propylene with a molecular state oxygen-containing gas. The gas mixture was introduced into an acrylic acid collection tower, and brought into contact with water to obtain an aqueous solution. The aqueous solution was introduced into an acrolein diffusion tower to diffuse acrolein, and to obtain an aqueous acrylic acid solution. The aqueous acrylic acid solution contained 65% by mass of acrylic acid, 30% by mass of water and 3.0% by mass of acetic acid. The aqueous acrylic acid solution was introduced into an azeotropic separation tower, and was subjected to azeotropic distillation using toluene as an azeotropic solvent. The azeotropic separation tower had sixty stages, and was equipped with sieve trays having stage intervals of 147 mm, a distillation pipe in the tower summit part, a raw material supply pipe in the center part, and a tower bottom liquid discharge pipe in the tower bottom part.

Concerning the operation state of the azeotropic separation tower at a normal operation, a tower summit temperature was 47° C., a tower bottom temperature was 99° C., a tower summit pressure was 100 mmHg, a reflux ratio, that is, total number of moles of refluxing solution per unit time/total number of moles of distilled solution per unit time, was 1.35, and a supply amount of the aqueous acrylic acid solution as a raw material solution was 7.62 L/h.

The distilled solution obtained from the tower summit of the azeotropic separation tower was led to a storage tank, and was separated into an organic phase containing toluene as a main component and a water phase. The organic phase was recycled into the azeotropic separation tower as a reflux solution.

As polymerization inhibitor, manganese acetate, dibutyldithiocarbamic acid copper salt, hydroquinone, phenothiazine and molecular-state oxygen were used. Manganese acetate, dibutyldithiocarbamic acid copper salt, hydroquinone and phenothiazine were introduced into the azeotropic separation tower through the tower summit. Molecular-state oxygen was introduced into the azeotropic separation tower through the tower bottom part. Manganese acetate, dibutyldithiocarbamic acid copper salt, hydroquinone and phenothiazine were respectively supplied in amounts of 50 ppm, 50 ppm, 100 ppm and 100 ppm, relative to the evaporated vapor amount of acrylic acid. The above-mentioned polymerization inhibitors were respectively dissolved in prescribed mother solutions to obtain respective solutions, which were introduced into the azeotropic separation tower by using a solution sending pump exclusively for each solution. Molecular state oxygen was supplied in an amount of 0.3% by volume to the evaporated vapor amount of acrylic acid.

A portion of the used dibutyldithiocarbamic acid copper salt (1 g) was well washed with water (100 mL). The copper ion concentration contained in the obtained washing water was measured by ICP emission analysis apparatus (manufactured by HORIBA, Ltd., ULTIMA), and was found to be 2.5 ppm. The copper ion amount contained in the washing water, which was calculated from the measured value of the copper ion concentration and the amount of the washing water, was 0.25 mg. It was assumed that the copper sulfate contained in the used dibutyldithiocarbamic acid copper salt was pentahydrate, and the ratio of copper sulfate contained in the portion of the dibutyldithiocarbamic acid copper salt was calculated from the copper ion amount and was found to be 980 ppm by mass. The dibutyldithiocarbamic acid copper salt was dissolved in a concentration of 3.5% by mass in the above reflux solution as a mother solution. The dibutyldithiocarbamic acid copper salt solution was supplied to the azeotropic separation tower. The content of the copper sulfate in the solution was 35 ppm by mass.

Manganese acetate and hydroquinone were dissolved in the aqueous acrylic acid solution as a mother solution to be supplied. In addition, phenothiazine was dissolved in the reflux solution as a mother solution to be supplied.

Concerning the composition of the mixed solution extracted from the tower bottom in a steady state, the ratio of acrylic acid was 97% by mass, acetic acid was 0.03% by mass, and other compound was 2.97% by mass. When continuous operation was carried out for 2 months under the condition, a constantly stable state was maintained. After the operation was terminated, the azeotropic separation tower was inspected; and as a result, generation of polymers was scarcely found. In addition, generation of precipitates in the line of the solution sending pump exclusively for the dibutyldithiocarbamic acid copper salt solution was not observed.

Example 2

An aqueous acrylic acid solution was subjected to azeotropic distillation operation in the same manner as Example 1, except that a solution of 8% by mass of dibutyldithiocarbamic acid copper salt was used. In accordance with the calculation of the copper sulfate content ratio in dibutyldithiocarbamic acid copper salt determined in Example 1, the dibutyldithiocarbamic acid copper salt solution contained 80 ppm by mass of copper sulfate.

When continuous operation was carried out for 2 months under the condition, a constantly stable state was maintained. After the operation was terminated, the azeotropic separation tower was inspected; and as a result, generation of polymers was scarcely found. However, generation of a little precipitates in the line of the solution sending pump exclusively for the dibutyldithiocarbamic acid copper salt solution was observed.

Comparative Example 1

An aqueous acrylic acid solution was subjected to azeotropic distillation operation in the same manner as Example 1, except that a solution of 12% by mass of dibutyldithiocarbamic acid copper salt was used. In accordance with the calculation of the copper sulfate content ratio in dibutyldithiocarbamic acid copper salt determined in Example 1, the dibutyldithiocarbamic acid copper salt solution contained 120 ppm by mass of copper sulfate.

When continuous operation was tried for 2 months under the condition, the line of the solution sending pump exclusively for the dibutyldithiocarbamic acid copper salt solution was clogged with precipitates during the operation, and thus it became impossible to send a prescribed amount of the dibutyldithiocarbamic acid copper salt solution. The operation was terminated on the 50th day and the azeotropic separation tower was inspected; and as a result, a large quantity of polymers was generated.

The above-mentioned results are shown in Table 1.

TABLE 1

| | CB solution | | | | Generation | |
| --- | --- | --- | --- | --- | --- | --- |
| | Copper sulfate content (ppm) | CB concentration (wt %) | Operation duration | Preparation or clogging | of polymers in tower | Remarkes |
| Example 1 | 35 | 3.5 | 2 months | None | Scarcerly generated | (1) |

TABLE 1-continued

|  | CB solution | | | | Generation | |
|---|---|---|---|---|---|---|
|  | Copper sulfate content (ppm) | CB concentration (wt %) | Operation duration | Preparation or clogging | of polymers in tower | Remarkes |
| Example 2 | 80 | 8 | 2 months | a little | Scarcerly generated | (2) |
| Comparative example 1 | 120 | 12 | 50 days | Occurred | Large quantity | |

CB: dibutyldithiocarbamic acid copper salt
(1): It was possible to further continuously carry out the operation.
(2): For further operation, washing of solution sending line for CB solution was needed.

As shown in the results of Comparative example 1, it became impossible to stably produce acrylic acid, in a case where the copper sulfate concentration in the dibutyldithiocarbamic acid copper salt solution supplied for suppressing the polymerization in the azeotropic separation tower was 120 ppm.

On the other hand, clogging of the solution sending pipe for the dibutyldithiocarbamic acid copper salt solution and generation of polymers in the azeotropic distillation tower could be suppressed and it was made possible to stably produce acrylic acid for a duration as long as 2 months, in a case where the copper sulfate concentration was adjusted to 100 ppm or lower.

The invention claimed is:

1. A method for inhibiting polymerization of (meth)acrylic acid and/or an ester thereof,
    comprising a step of inhibiting polymerization of (meth) acrylic acid and/or the ester thereof by using a solution of a dialkyldithiocarbamic acid copper salt dissolved in an organic solvent,
    wherein the content amount of copper sulfate in the solution of the dialkyldithiocarbamic acid copper salt is 100 ppm or less by mass.

2. The polymerization inhibition method according to claim 1, wherein a concentration of the dialkyldithiocarbamic acid copper salt in the solution of the dialkyldithiocarbamic acid copper salt is 0.1% or more by mass and 10% or less by mass.

3. The polymerization inhibition method according to claim 1, wherein the dialkyldithiocarbamic acid copper salt is at least one selected from a group consisting of dimethyldithiocarbamic acid copper salt, diethyldithiocarbamic acid copper salt, dipropyldithiocarbamic acid copper salt and dibutyldithiocarbamic acid copper salt.

4. The polymerization inhibition method according to claim 2, wherein the dialkyldithiocarbamic acid copper salt is at least one selected from a group consisting of dimethyldithiocarbamic acid copper salt, diethyldithiocarbamic acid copper salt, dipropyldithiocarbamic acid copper salt and dibutyldithiocarbamic acid copper salt.

* * * * *